United States Patent [19]

Taylor et al.

[11] Patent Number: 4,833,145

[45] Date of Patent: May 23, 1989

[54] 4(3H)-OXO-5,6,7,8-TETRAHYDROPYRIDO[2,3-d]PYRIMIDINE DERIVATIVES

[75] Inventors: Edward C. Taylor, Princeton, N.J.; George P. Beardsley, Essex, Conn.; Chuan Shih, Indianapolis, Ind.

[73] Assignees: The Trustees of Princeton University, Princeton, N.J.; Eli Lilly and Company, Indianapolis, Ind.

[21] Appl. No.: 120,360

[22] Filed: Nov. 13, 1987

Related U.S. Application Data

[63] Continuation-in-part of Ser. No. 879,935, Jun. 30, 1986, abandoned.

[51] Int. Cl.$^4$ ............... A61K 31/505; C07D 471/04
[52] U.S. Cl. ........................... 514/258; 544/279
[58] Field of Search .............. 544/279, 225, 226; 514/258, 186

[56] References Cited

U.S. PATENT DOCUMENTS

| | | | |
|---|---|---|---|
| 3,856,959 | 12/1974 | Mead | 424/251 |
| 4,172,200 | 10/1979 | Piper et al. | 544/260 |
| 4,369,319 | 1/1983 | DeGraw et al. | 544/260 |
| 4,431,805 | 2/1985 | Temple et al. | 544/279 |
| 4,432,981 | 2/1984 | Lesher et al. | 424/251 |
| 4,460,591 | 7/1984 | DeGraw et al. | 424/251 |
| 4,512,992 | 4/1985 | Duch et al. | 514/258 |
| 4,526,964 | 7/1985 | Temple et al. | 544/279 |
| 4,532,241 | 7/1985 | DeGraw et al. | 514/258 |
| 4,536,575 | 8/1985 | Temple et al. | 544/279 |
| 4,564,616 | 1/1986 | Jones et al. | 514/260 |
| 4,684,653 | 8/1987 | Taylor et al. | 544/279 |
| 4,725,687 | 2/1988 | Piper et al. | 544/279 |

FOREIGN PATENT DOCUMENTS

1534238 11/1978 United Kingdom .

OTHER PUBLICATIONS

Harrington, Synthetic Approaches to 5- Deaza and 5,10- Dideaza Folic Acid Analogs, Ph.D. Dissertation, Princeton U., 1982.
Moad et al., Jacs 101:20, 6068-6076 (9/27/76).
Jahine et al., Ind. J. Chem., 16B, 889-891 (10/78).
Sirotnak et al., Cancer Treat. Rep., 66:2 (2/82).
Troschütz et al., Arch. Pharm. 311, 406-414 (1978).
Temple et al., J. Org. Chem 47, 761-764 (1982).
Taylor et al., Chem. & Biology of Pteridines (Ed. J. A. Blair) Walter de Gruyter & Co., N.Y. 115-119 (1983).
Taylor et al., J. Org. Chem. 48, 4852-4860 (1983).
Taylor et al., J. Org. Chem. 50, 1005-1014 (1985).
DeGraw et al., J. Heterocycl. Chem. 19, 1461-1463 (1982).
Grivsky et al., J. Med. Chem. 23:3, 327-329 (1980).
Piper et al., J. Med. Chem. 23, 320-321 (1980).
DeGraw et al., J. Med. Chem 17:5, 552-553 (1974).
Elliott et al., J. Med. Chem. 17:5, 553-555 (1974).
Nair, J. Org. Chem., 50, 1879-1884 (1985).
Drugs of the Future, IV, No. 9, 641-644 (1979).
Sirotnak et al., Cancer Treat. Rep. 62:7, 1047-1052 (1978).
Stone et al., Biochem. Pharmac. 33:2, 175-179 (1984).
Srinivasan et al., J. Org. Chem., 45, 3746-3748 (1980).
Hurlbert et al., J. Med. Chem., 11, 703-717 (1968).
Rosowsky et al., J. Med. Chem., 17:12, 1872-1276 (1974).
Struck et al., J. Med. Chem., 14:8, 693-695 (1971).
CA 96:104757a Sirotnak et al. (1982).
Taylor et al., J. Med. Chem. 28:7, 914-921 (1985).
DeGraw et al., J. Heterocycl. Chem. 8, 105-110 (1971).
Oakes et al., J. Chem. Soc. (London) 4433 (1956).
Elslager et al., Lectures in Heterocyclic Chemistry, vol. 2, S-97; Supplement to J. Heterocyclic Chem., 11 (1974).
DeGraw et al. (VII), J. Med. Chem., 17:470 (1974).
DeGraw et al. (VIII), J. Heterocyclic Chem., 13:439 (1976).
Smith et al., Biochem. 20: 1241 (1981).
Temple et al. (V), J. Med. Chem. 24: 1254 (1981).
DeGraw et al. (IX), Chem. & Biolog. of Pteridines (Ed. Kisliuk/Brown) Elsevier, North Holland (229-234) (1979).
Srinivasan et al. (II), J. Org. Chem. 46: 1777 (1981).
Srinivasan et al. (III), Tetrahedron Lett. 23:1431 (1982).
DeGraw et al. (X), PCT Application WO85/02844 (Published Jul. 4, 1985).
Wheeler et al., J. Amer. Chem. Soc. 74:4725 (1952).
Kisliuk, R. L., Nature, 188:584 (1960).
Kisliuk et al. (II), J. Biol. Chem. 239: 1900 (1964).
Horwitz et al., J. Med. Chem. 11:907 (1968).

*Primary Examiner*—Donald G. Daus
*Assistant Examiner*—E. Bernhardt
*Attorney, Agent, or Firm*—Bruce M. Collins

[57] ABSTRACT

Derivatives of N-[4-(N-[2-amino-4(3H)-oxo-5,6,7,8-tetrahydropyrido[2,3-d]pyrimidin-6-ylmethyl]-amino)benzoyl]-L-glutamic acid are antineoplastic agents. Their preparation and use, and intermediates useful for their preparation are described.

10 Claims, No Drawings

4(3H)-OXO-5,6,7,8-TETRAHYDROPYRIDO[2,3-D]PYRIMIDINE DERIVATIVES

TECHNICAL FIELD

The invention pertains to derivatives of N-[4-(N-[2-amino-4(3H)-oxo-5,6,7,8-tetrahydropyrido-[2,3-d]pyrimidin-6-ylmethyl]amino)benzoyl]-L-glutamic acid, which derivatives are antineoplastic agents, to their preparation and use, and to intermediates useful in their preparation.

BACKGROUND ART

The folic acid antimetabolites aminopterin and amethopterin (also known as 10-methylaminopterin or methotrexate) are antineoplastic agents. These compounds inhibit enzymatic conversions involving metabolic derivatives of folic acid. Amethopterin, for example, inhibits dihydrofolate reductase, an enzyme necessary for the regeneration of tetrahydrofolate from the dihydrofolate which is formed during the conversion of 2-deoxyuridylate to thymidylate by the enzyme thymidylate synthetase.

Other derivatives of folic acid and aminopterin have been synthesized and tested as antimetabolites. Among these are compounds in which a methylene or methylidene group occupies a position in the molecule normally occupied by an imino or nitrilo group, respectively. These derivatives have varying degrees of antimetabolic activity. 10-Deazaaminopterin is highly active (Sirotak et al., *Cancer Treat. Rep.*, 1978, 62, 1047) and 5-deazaaminopterin has activity similar to that of amethopterin (Taylor et al., *J. Org. Chem.*, 1983, 48, 4852). 8,10-Dideazaaminopterin is reported to be active (U.S. Pat. No. 4,460,591) and 5,8,10-trideazaaminopterin exhibits activity against mouse L1210 leukemia (Yan et al., *J. Heterocycl. Chem.*, 1979, 16, 541). 10-Deazfolic acid, on the other hand, shows no significant activity (Struck et al., *J. Med. Chem.*, 1971, 14, 693) and 5-deazafolic acid is only weakly cytotoxic. 8,10-Dideazafolic acid is only marginally effective as a dihydrofolate reductase inhibitor (De Graw et al., "Chemistry and Biology of Pteridines", Elsevier, 1979, 229) and 5,8,10-trideazafolic acid also shows only marginal activity against mouse L1210 leukemia (Oatis et al., *J. Med. Chem.*, 1977, 20, 1393). 5,10-Dideazaaminopterin and 5,10-dideaza-5,6,7,8-tetra-hydroaminopterin, and the corresponding 5,10-dideazafolic acid derivatives are reported by Taylor et al., *J. Med. Chem.*, 28:7, 914 (1985).

DISCLOSURE OF INVENTION

The invention pertains to (i) 4(3H)-oxo-5,6,7,8-tetrahydropyrido[2,3-d]pyrimidines of the formula:

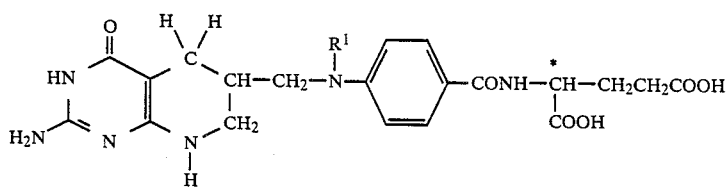

wherein:

$R^1$ is hydrogen, methyl, or ethyl; and the configuration about the carbon atom designated * is L; (ii) the tautomeric forms thereof; and (iii) the pharmaceutically acceptable alkali metal, alkaline earth, non-toxic metal, ammonium, and substituted ammonium salts thereof.

The invention also pertains to methods for the preparation of such compounds, to intermediates useful in those preparations, and to methods and compositions for the use of such compounds in combating neoplastic growth.

MODES FOR CARRYING OUT THE INVENTION

The compounds of the invention are derivatives of the 5,6,7,8-tetrahydropyrido[2,3-d]pyrimidine heterocyclic ring which is numbered as follows:

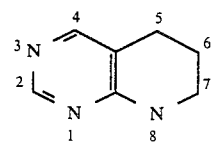

The compounds of Formula I exist in tautomeric equilibrium with the corresponding 4-hydroxy compounds:

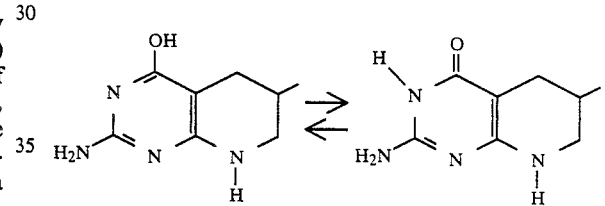

For convenience, the 4(3H)-oxo form is depicted and the corresponding nomenclature is used throughout this specification, it being understood that in each case such includes the tautomeric 3,4-dehydro-4-hydroxy form.

Two chiral centers are present in the final molecule: the carbon atom in the 6-position of the tetrahydropyrido[2,3-d]pyrimidine ring and the alpha carbon atom in the glutamic acid group. Of the theoretical four forms of the compound, the use of a protected N-(4-aminobenzoyl)-L-glutamic acid reagent in the preparation of a compound of Formula III reduces the possibilities to two. Both of these, however, are generated during the subsequent hydrogenation to a compound of Formula III and consequently, upon removal of the protecting groups, the desired compound is produced as a mixture of the (S,S) and (R,S) diastereoisomers. These can be represented for the compound in which $R^{2'}$, $R^{3'}$ and $R^{4'}$ are all hydrogen as follows:

(S,S): 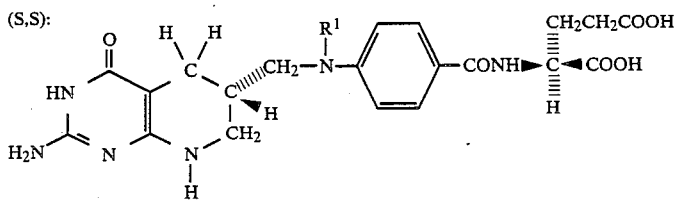

(R,S): 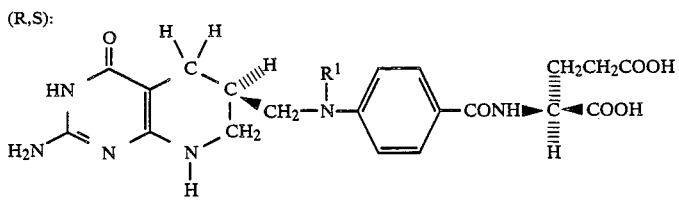

These diastereoisomers can be separated mechanically, as by chromatography, so that each is in a form substantially free of the other; i.e., having an optical purity of >95%. Alternatively, a mixture of diastereoisomeric compounds of Formula I is treated with a chiral acid operable to form a salt therewith. The resultant diastereoisomeric salts are then separated through one or more fractional crystallizations and thereafter the free base of the cationic moiety of at least one of the separated salts is liberated through treatment with a base and removal of the protecting groups. The liberation of the cation of the salt can be performed as a discrete step before or after the removal of the protecting groups, or concomitantly with the removal when such groups are susceptible to removal under basic conditions; i.e., basic hydrolysis.

Suitable chiral acids include the individual enantiomers of 10-camphorsulfonic acid, camphoric acid, alpha bromocamphoric acid, menthoxyacetic acid, tartaric acid, diacetyltartaric acid, malic acid, pyrrolidone-5-carboxylic acid, and the like.

The invention includes the pharmaceutically acceptable alkali metal, alkaline earth metal, non-toxic metal, ammonium, and substituted ammonium salts, such as for example the sodium, potassium, lithium, calcium, magnesium, aluminum, zinc, ammonium, trimethylammonium, triethylammonium, triethanolammonium, pyridinium, substituted pyridinium, and the like.

The compounds of this invention have an effect on one or more enzymes which utilize folic acid, and in particular metabolic derivatives of folic acid, as a substrate.

The compounds can be prepared in a first process by hydrolysis or hydrogenolysis of a 2-amino-4(3H)-oxo-5,6,7,8-tetrahydropyrido[2,3-d]pyrimidinyl-L-glutamic acid derivative of the formula:

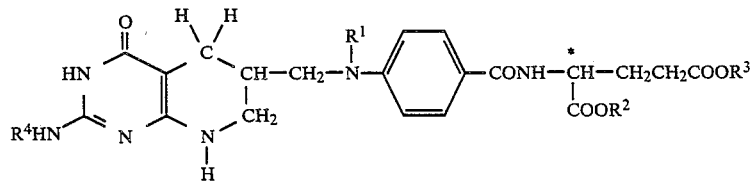

wherein
$R^1$ is as defined above;
$R^2$ and $R^3$ are the same or different carboxylic acid protecting group;

$R^4$ is an amino protecting group; and the configuration about the carbon atom designated * is L.

Protecting groups encompassed by $R^2$, $R^3$ and $R^4$ and reactions for their removal are described, for example, in "Protective Groups in Organic Chemistry", Plenum Press, London and New York (1973); Greene, "Protective Groups in Organic Synthesis", Wiley, New York (1981); "The Peptides", Vol. I, Schroder and Lubke, Academic Press, London and New York (1965); in "Methoden der organischen Chemie", Houben-Weyl, 4th Edition, Vol. 15/I, Georg Thieme Verlag, Stuttgart (1974).

Carboxylic acid protecting groups can be, for example, ester conceptually derived from lower alkanols of from 1 to 6 carbon atoms, including those branched in the 1-position and those which are substituted with one or more aromatic groups such as phenyl, or with halo or alkoxy; e.g., methyl, ethyl, t-butyl, benzyl, 4-nitro-benzyl, diphenylmethyl, methoxymethyl, and the like esters. Silyl esters such as trimethylsilyl also can be employed.

Amino protecting groups include acyl, notably alkanoyl of 2 to 6 carbon atoms and alkoxycarbonyl, either of which may be substituted with halo, alkoxy, or phenyl (e.g., acetyl, 2,2,2-trichloroacetyl, t-butoxy-carbonyl); benzoyl; 4-nitrobenzyloxycarbonyl, and the like.

The hydrolysis is conducted at normal temperatures utilizing aqueous acid or base, such as for example, an aqueous alkali metal hydroxide, optionally in the presence of a water miscible organic solvent such as methanol, ethanol, tetrahydrofuran, dimethylformamide, and the like, or an acid, as for example trifluoroacetic acid. When base is used, the product is initially formed as the dicationic glutamate salt and can be readily precipitated by adjustment of pH, as through acidification with, for example, acetic acid. The resulting products generally are high melting crystalline or microcrystalline solids.

The compounds of Formula I alternatively can be prepared, as can the glutamic acid intermediate of Formula II, by hydrogenating a pyrido[2,3-d]pyrimidine compound of the formula:

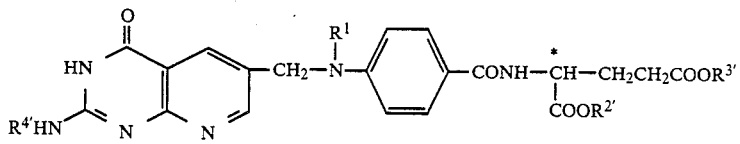

in which $R^1$ is as defined above; each of $R^{2'}$, $R^{3'}$ is hydrogen or a carboxylic acid protecting group as defined above for $R^2$ and $R^3$ and $R^{4'}$ is hydrogen or an amino protecting group as defined above for $R^4$.

The hydrogenation is conducted in an acidic medium in the presence of a noble metal catalyst such as platinum, ruthenium or rhodium, including the oxides thereof and the supported forms thereof. The preferred catalyst is platinum oxide. Conditions of time, temperature, and pressure are selected so that reduction of the pyridine ring is achieved without involvement of the pyrimidine ring. With platinum oxide, for example, the desired product is obtained in about 15 minutes utilizing ambient temperatures and a hydrogen pressure of 50 to 60 psi.

When $R^{2'}$, $R^{3'}$ and $R^{4'}$ are hydrogen, the product of this reduction will be a compound of Formula I. If all $R^{2'}$, $R^{3'}$, and $R^{4'}$ are other than hydrogen, the product will be a compound of Formula II.

Compounds of Formula III are known or can be prepared by conventional procedures. For example, 2-amino-4(3H)-oxo-6-formylpyrido[2,3-d]pyrimidine can be treated with an appropriate reagent to introduce the $R^4$ protecting group, such as acetic anhydride, and the resulting product allowed to react with a protected N-(4-aminobenzoyl)-L-glutamic acid derivative to yield the compound of Formula III herein in which $R^1$=H [see e.g., Taylor et al., J. Org. Chem., 48, 4852 (1983)]. Utilization of the corresponding N-(4-methylaminobenzoyl)-L-glutamic acid or N-(4-ethylaminobenzoyl)-L-glutamic acid yields the corresponding compound of Formula III in which R' is methyl or ethyl, respectively.

The compounds of Formula I can be used, alone or in combination, to treat neoplasms which in the past have been treated with methotrexate, including choriocarcinoma, leukemia, adenocarcinoma of the female breast, epidermid cancers of the head and neck, squamous or small-cell lung cancer, and various lymphosarcomas. In representative models for example, N-[4-(N-[2-amino-4(3H)-oxo-5,6,7,8-tetrahydropyrido[2,3-d]-pyrimidin-6-ylmethyl]amino)benzoyl]-L-glutamic acid exhibited an IC$_{50}$ of 0.005–0.007 (2.2×10$^{-8}$ molar) against CCRF-CEM cell lines (a human T-cell derived leukemia). The diastereoisomers thereof, herein designated "A" and "B", exhibited IC$_{50}$'s of 0.0026 and 0.0027 mcg/ml, respectively. 5-Deazafolic acid on the other hand is relatively inactive in this test. The compounds can also be used to treat mycosis fungoides and psoriasis.

The compounds may be administered either orally or preferably parenterally, alone or in combination with other anti-neoplastic agents, steroids, etc., to a mammal suffering from neoplasm and in need of treatment. Parenteral routes of administration include intramuscular, intrathecal, intravenous or intra-arterial. In general, the compounds are administered in much the same fashion as methotrexate, but because of a different mode of action, can be administered in higher dosages than those usually employed with methotrexate Leucovorin rescue is not needed. Dosage regimens must be titrated to the particular neoplasm, the condition of the patient, and the response but generally doses will be from about 10 to about 100 mg/day for 5–10 days or single daily administration of 250–500 mg, repeated periodically; e.g., every 14 days. Oral dosage forms include tablets and capsules containing from 1–10 mg of drug per unit dosage. Isotonic saline solutions containing 20–100 mg/ml can be used for parenteral administration.

The following examples will serve to further illustrate the invention.

EXAMPLE 1

Diethyl N-[4-(N-[2-acetamido-4(3H)-oxopyrido[2,3-d]-pyrimidin-6-ylmethyl]amino) benzoyl]glutamate A mixture of 800 mg of 2-acetamido-6-formyl-4(3H)-oxopyrido[2,3-d]pyrimidine [Taylor et al. J. Org. Chem. 48, 4852 (1983)] in 55 ml of glacial acetic acid and 1.2 g of diethyl p-aminobenzoyl-L-glutamate is allowed to stand at room temperature for 5 hours. To the mixture is then added 0.19 ml of boron hydride:triethylamine complex. This mixture is stirred for 40 minutes at room temperature and then heated to 60° C. for 10 minutes. The reaction mixture is cooled, and concentrated in vacuo. The resulting residue is dissolved in 90 ml of methanol, and the solution filtered. The solid which is collected is washed with 20 ml of methanol and 360 ml of ether. The filtrates are combined and evaporated to dryness. The residue is flash chromatographed [see Still et al., J. Org. Chem., 43, 2923 (1978)] over silica (97:3 chloroform:methanol) to yield 1.08 g of diethyl N-[4-(N-[2-acetylamino-4(3H)-oxopyrido[2,3-d]-pyrimidin-6-ylmethyl]amino)benzoyl]-L-glutamate.

EXAMPLE 2

Diethyl N-[4-(N-[2-acetamido-4(3H)-oxo-5,6,7,8-tetrahydropyrido[2,3-d]pyrimidin-6-ylmethyl]amino)benzoyl]-L-glutamate A mixture of 340 mg of diethyl N-[4-(N-[2-acetylamino-4(3H)-oxopyrido[2,3-d]pyrimidin-6-ylmethyl]-amino)benzoyl]-L-glutamate in 80 ml of methanol and 40 ml of glacial acetic acid is placed in the vessel of a hydrogenation apparatus (Adams). Fifty-five milligrams of platinum oxide catalyst are added and the mixture is hydrogenated at 60 psi at room temperature for 15 minutes. The catalyst is removed by filtration, and the filtrate concentrated in vacuo. The residue is flash chromatographed over silica with chloroform:methanol gradients (97:3 to 95.5:5), collecting 20 ml fractions. Fractions 62–73 contain a by-product, 2-acetylamino-6-methyl-4(3H)-oxopyrido[2,3-d]pyrimidine. Fractions 74–88 contain 15.4 mg. of the desired product, diethyl N-[4-(N-[2-actylamino-4(3H)-oxo-5,6,7,8-tetrahydropyrido[2,3-d]pyrimidin-6ylmethyl-]amino)benzoyl]-L-glutamate.

EXAMPLE 3

N-[4-(N-[2-amino-4(3H)-oxo-5,6,7,8-tetrahydropyrido-[2,3-d]pyrimidin-6-ylmethyl]amino)benzoyl]-L-glutamic acid Twenty milligrams of diethyl N-[4-(N-[2-acetylamino-4(3H)-oxo-5,6,7,8-tetrahydropyrido[2,3-d]-pyrimidin-6-ylmethyl]amino)benzoyl]-L-glutamate are dissolved in 8 ml of methanol and 0.4 ml of 1.0 N aqueous sodium hydroxide are added. The mixture is stirred at room temperature for 96 hours and 0.1 ml of glacial acetic acid is then added. The methanol is removed in vacuo and the resulting residue is dissolved in 5 ml of water. This mixture is acidified with 0.16 ml of glacial acetic and the solution which forms is collected by filtration to yield 6.0 mg. of product; N-[4(N-[2-amino-4(3H)-oxo-5,6,7,8-tetrahydropyrido[2,3-d]-pyrimidin-6-6-ylmethyl]amino)benzoyl]-L-glutamic acid, mass spectrum at 444; m.p. with decomposition beginning at 198° C.; $^1$H NMR (Me$_2$SO-d$_6$) delta 1.86–2.1 (m, 6H), 2.31 (t, 2H, J=7.2), 2.8–2.86 (m, 1H), 3.24–3.28 (m, 2H), 4.2–4.4 (m, 1H), 5.94 (s, 2H), 6.29 (s, 1H), 6.34 (t, 1H, J=5.24), 6.56–6.58 (AA'BB', 2H), 7.62–7.65 (AA'BB', 2H), 8.06 (d, J=5.15), 9.7 (br, s, 1H).

EXAMPLE 4

A 1 mg/ml solution of N-[4-(N'-[2-amino-4(3H)-oxo-5,6,7,8-tetrahydropyrido[2,3-d]pyrimidin-6-ylmethyl-]amino)benzoyl]-L-glutamic acid in 15% acetonitrile and 85% of a 0.1% solution of triethylamine-acetic acid (buffered to pH 7.0) is prepared. This solution is introduced into a 10 mm×50 cm Cyclobond I reverse phase HPLC column utilizing the same solvent system. A flow rate of 1.10 ml/min is employed with UV monitoring at 254 nm.

A first diastereoisomer substantially free of the other is obtained at a retention time of 45.58 minutes, herein designated Isomer "A". The second diastereoisomer substantially free of the first is obtained at a retention time of 48.32 minutes, herein designated Isomer "B". Both diastereoisomers show a UV peak at 283 nm.

What is claimed is:

1. A compound selected from the group consisting of:
   (i) 4(3H)-oxo-5,6,7,8-tetrahydropyrido[2,3-d]-pyrimidines of the formula:

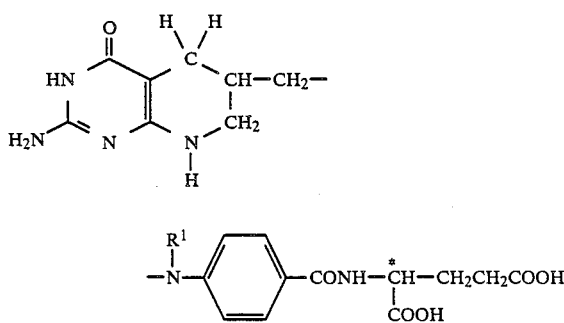

wherein:
   R$^1$ is hydrogen, methyl, or ethyl; and
   the configuration about the carbon atom designated * is L;
   (ii) the tautomeric forms thereof; and
   (iii) the pharmaceutically acceptable alkali metal, alkaline earth, non-toxic metal, ammonium, and substituted ammonium salts thereof.

2. The compound according to claim 1 wherein R$^1$ is hydrogen.

3. The (S,S) diastereoisomer of the compound according to claim 2 and having the following absolute configuration:

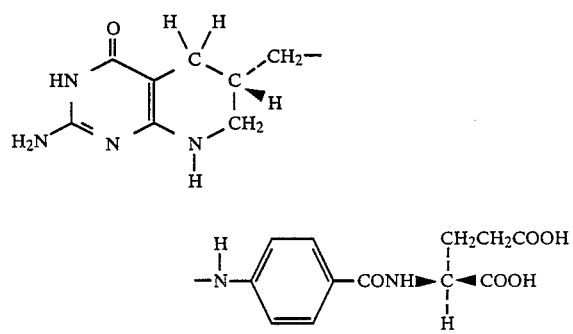

4. The (R,S) diastereoisomer of the compound according to claim 2 and having the following absolute configuration:

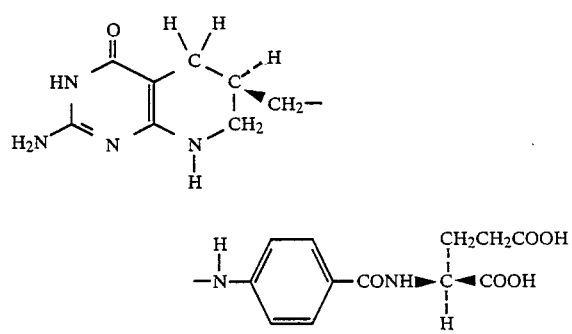

5. The compound according to claim 1 wherein R$^1$ is methyl.

6. The method of combating neoplastic growth in a mammal which comprises administering to the mammal in a single or multiple dose regimen an effective amount of a compound according to claim 1.

7. A pharmaceutical composition for combating neoplastic growth in a mammal which comprises an amount of a compound according to claim 1 which upon administration to the mammal in a single or multiple dose regimen is effective to combat said growth, in combination with a pharmaceutically acceptable carrier.

8. A compound selected from the group consisting of:
   (i) 4(3H)-oxo-5,6,7,8-tetrahydropyrido[2,3-d]pyrimidines of the formula:

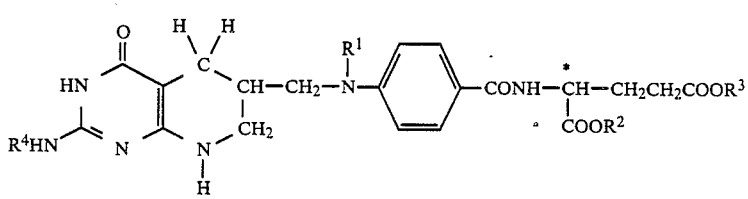

wherein
R¹ is hydrogen, methyl, or ethyl;
R² and R³ are the same or different carboxylic acid protecting group selected from the group consisting of alkyl of 1 to 6 carbon atoms, unsubstituted or substituted with one or more of phenyl, halo, or alkoxy; and silyl;
R⁴ is an amino protecting group selected from the group consisting of alkanoyl or alkoxycarbonyl of 2 to 6 carbon atoms, unsubstituted or substituted with one or more phenyl, halo, or alkoxy; benzoyl; and 4-nitrobenzoyloxycarbonyl; and
the configuration about the carbon atom designated * is L; and
(ii) the tautomeric forms thereof.

9. A compound according to claim 8 wherein each of R² and R³ is alkyl of 1 to 6 carbon atoms and R⁴ is alkanoyl of 2 to 6 carbon atoms.

10. The compound according to claim 9 in which R¹ is hydrogen, each of R² and R³ is ethyl, and R⁴ is acetyl or pivaloyl.

* * * * *